(12) United States Patent
Liang et al.

(10) Patent No.: US 10,227,363 B2
(45) Date of Patent: Mar. 12, 2019

(54) POLYMER WITH ALTERNATING PHENYLENE SILICON AND SILOXANE STRUCTURE AND METHOD OF PRODUCING PRECURSOR OF THE SAME

(71) Applicant: NATIONAL CHUNG SHAN INSTITUTE OF SCIENCE AND TECHNOLOGY, Taoyuan (TW)

(72) Inventors: Chao-Fan Liang, Taoyuan (TW); Chih-Min Hsieh, Taoyuan (TW); Jui-Chang Tseng, Taichung (TW); Qi-Qian Tan, Taichung (TW)

(73) Assignee: NATIONAL CHUNG SHAN INSTITUTE OF SCIENCE AND TECHNOLOGY (TW)

( * ) Notice: Subject to any disclaimer, the term of this patent is extended or adjusted under 35 U.S.C. 154(b) by 4 days.

(21) Appl. No.: 15/407,602

(22) Filed: Jan. 17, 2017

(65) Prior Publication Data
US 2018/0201631 A1    Jul. 19, 2018

(51) Int. Cl.
*C07F 7/18* (2006.01)
*C07F 7/08* (2006.01)
*C08G 77/06* (2006.01)
*C08G 77/00* (2006.01)

(52) U.S. Cl.
CPC .......... *C07F 7/0836* (2013.01); *C08G 77/06* (2013.01); *C08G 77/80* (2013.01)

(58) Field of Classification Search
CPC .................................................. C07F 7/0836
See application file for complete search history.

(56) References Cited

U.S. PATENT DOCUMENTS

| | | | | |
|---|---|---|---|---|
| 2,561,429 A | * | 7/1951 | Sveda | C07F 7/0836 556/432 |
| 3,135,777 A | * | 6/1964 | Nielsen | C08G 77/52 528/12 |
| 3,202,634 A | * | 8/1965 | Merker | C08G 77/00 528/35 |
| 3,209,018 A | * | 9/1965 | Merker | B01J 31/02 556/432 |
| 3,338,870 A | * | 8/1967 | Buchheit | C07F 7/0834 528/14 |
| 3,646,013 A | * | 2/1972 | Ercoli et al. | C07J 71/00 540/92 |
| 3,965,134 A | * | 6/1976 | LaRochelle | C07F 7/0836 556/432 |

* cited by examiner

*Primary Examiner* — Margaret G Moore
(74) *Attorney, Agent, or Firm* — Schmeiser, Olsen & Watts, LLP

(57) ABSTRACT

A polymer with alternating phenylene silicon and siloxane structure and a method of producing a precursor of the same are introduced to develop an autonomous synthesis process for para-phenylene disilanol monomer compounds and design a technique of purifying the polymer with alternating phenylene silicon and siloxane structure easily, so as to enable mass production of the polymer with alternating phenylene silicon and siloxane structure.

9 Claims, 8 Drawing Sheets

POLYMER WITH ALTERNATING PHENYLENE SILICON AND SILOXANE STRUCTURE AND METHOD OF PRODUCING PRECURSOR OF THE SAME

FIELD OF THE INVENTION

The present invention relates to halogen-free non-inflammable silicone polymers and methods of producing the same and, more particularly, to a polymer with alternating phenylene silicon and siloxane structure and a method of producing a precursor of the same.

BACKGROUND OF THE INVENTION

According to the prior art, a non-inflammable agent is an important additive to a polymer and is intended to modify the combustibility of inflammable materials and thereby enhance the capability of the polymer to be non-inflammable, spontaneously stop burning, and not emit smoke, thereby preventing the polymer from staying active and spreading. Conventional halogen-containing non-inflammable agents in wide use display high efficiency of flame retardation, incur low manufacturing costs, and are highly compatible with the other related materials. But, when burning, conventional halogen-containing non-inflammable agents in wide use undergo decomposition to thereby produce highly toxic, corrosive gases and emit thick smoke to the detriment of public health and environmental protection. With environmental awareness on the rise, green legislations are enacted by governments to ban halogen-containing non-inflammable agent, thereby justifying the urgency and necessity of development of halogen-free non-inflammable agents.

Halogen-free silicon-containing non-inflammable agents are advantageously non-toxic and emit little smoke, but inorganic silicon-containing non-inflammable agents sometimes exhibit incompatibilities with polymer substrates and therefore cause the detriment of the physical properties and processibility of polymer substrates. As a result, polymer substrates must contain the other additive or filler in order to effectuate optimal flame retardation. By contrast, organic silicone-containing non-inflammable agents are non-toxic, prevent melt drops and emit little smoke during combustion, display high flame retardation efficiency, are environmentally friendly for being halogen-free, and thus have a more promising future applicability.

Depending on their constituent groups, silicone non-inflammable agents fall into two categories: organosiloxane and silicone rubber. The two categories differ slightly in the main chain structure. The main chain of organosiloxane consists of repeating —R2Si—O— bonds, wherein silicon atoms are substituted with saturated alkyl, vinyl, phenyl or the other organic groups. Furthermore, organosiloxane often mixes with an additive or filler, such as aluminum hydroxide to enhance its non-inflammable property, albeit at the cost of material compatibility and processibility, not to mention ending up with the following disadvantages: releasing water from its hydrated complex at high temperature, generating bubbles inside the polymeric material to the detriment of appearance, and deteriorating the capability of the material to be waterproof and electrically insulating.

Like organosiloxane, the main chain of silicone rubber consists of repeating Si—O—Si bonds, wherein silicon atoms are attached with saturated alkyl, vinyl, phenyl or the other organic groups. By contrast, the main chain of silicone rubber usually builds with rigid organic aryl groups, such as phenylene, to increase the insulating charring layer content generated during combustion, and in consequence a dense and stable silicon-containing charring protective layer will be formed firmly on the surface of the substrate in order to block external heat and oxygen, so as to prevent the polymer material from undergoing thermal degradation or producing inflammable volatile substances, and prevent melt drops during combustion.

Both silicone rubber and its elastomer are non-toxic, prevent melt drops upon combustion, emit little smoke, display high flame retardation efficiency, and are thermally stable, electrically insulating, resistant to chemicals, waterproof, and oil-proof. Therefore they are applicable to various industrial hermetic seal materials, non-inflammable materials, heat resistant materials, plastic materials, coating materials, packing materials, adhering glues, electrically insulated products, medical equipment for heat-resistant sterilization, and artificial films.

MacKnight and others performed polycondensation with recrystallized para-phenylene disilanol and high-purity diamino silane to produce a polymer with alternating para-phenylene silicon and siloxane structure. The polymer thus produced is tested by thermal analysis, and the molecular weight of the polymer is analyzed by gel permeation chromatography (GPC); the results show that the process method produces a thermally-satisfactory non-inflammable polymer from a silicone rubber elastomer. However, the polymer produced by the method incurs high processing costs, and the technique of separation and purification is not suitable for mass production. Furthermore, the polymer with alternating para-phenylene silicon and siloxane structure mostly exists in the form of a highly viscous liquid gel or an elastomer, as with the filtration and collection techniques of the method disclosed in the prior art, showing that the conventional method fails to separate and purify the polymer efficiently and in a high yield.

The monomer compounds, such as para-phenylene disilanol and dimethylaminosilane, required for producing the polymer are pricey. The production of the polymer necessitates intricate processing and reaction steps. As a result, the production of the polymer is not suitable for mass production. Furthermore, MacKnight and others disclosed that, when purchased commercially, the compound which consists of para-phenylene disilanol monomer requires undergoing additional recrystallization and purification processes which involve using internationally banned and toxic carbon tetrachloride as a recrystallizing solvent to the detriment of industrial development and environmental sustainability. Another solvent which has ever been used in recrystallization and purification processes is toluene which dissolves para-phenylene disilanol monomer compounds to a certain extent, thus fails to meet the requirements for the purification process and recycling rate of the monomer compounds. To avoid using expensive commercially available monomer sources, the prior art discloses that synthesis process of para-phenylene disilanol monomer compounds entails performing alkoxide substitution reaction with para-phenylene disilane precursor and then performing hydrolysis, so as to produce the para-phenylene disilanol monomer compounds. The solvent for use in the process is a mixture of absolute ethanol and anhydrous tetrahydrofuran. For the perspective of industrial applications, since the production of absolute ethanol is pricier than that of methanol, its selling prices are high, and thus its usage cannot reduce process costs significantly.

Furthermore, the prior art discloses that the treatment process of the para-phenylene disilanol monomer compounds not only requires effectuating neutralization with a potassium dihydrogen phosphate buffered solution, but also entails performing an intricate aqueous solution treatment process and product purification process, and its separation and purification techniques are not feasible for mass production, which produce excessive process wastes, incur high process costs, lack industrial applicability and mass production feasibility.

Therefore, it is an objective of the present invention to overcome the aforesaid drawbacks which confront the reaction process as well as separation and purification processes and promote the industrial applications for non-inflammable silicone polymer materials by developing a polymer with alternating phenylene silicon structure and siloxane structure and a precursor thereof.

Accordingly, it is imperative to provide a polymer with alternating phenylene silicon and siloxane structure and a method of producing a precursor of the same and develop an autonomous synthesis process of phenylene disilanol monomers for direct use in a subsequent polymerization reaction, without performing any additional purification and separation processes. Furthermore, it is imperative to provide a simple method of producing the polymer as well as separation and purification processes thereof to thereby effectuate ease of process and attain economic benefits, thus producing a polymer which comprises phenylene silicon and siloxane and meets industrial needs.

SUMMARY OF THE INVENTION

In view of the aforesaid drawbacks of the prior art, it is an objective of the present invention to provide a method of producing a phenylene disilanol precursor monomer and a method of producing, separating, and purifying a polymer with alternating phenylene silicon and siloxane structure. Specifically speaking, the present invention provides a method of producing a para-phenylene disilanol monomer compound, characterized in that the method is based on an autonomous synthesis process which uses cheap raw reactants, incurs low development and processing costs, entails following simple steps, requires no banned solvents, enables mass production, and applies to halogen-free non-inflammable silicon rubber manufacturing. The present invention further provides a simple way of processing, separating, and purifying a polymer with alternating phenylene silicon structure and siloxane structure.

In order to achieve the above and other objectives, the present invention provides a phenylene disilanol expressed by structural formula (I):

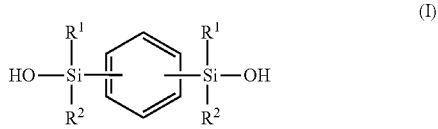

wherein $R^1$ and $R^2$ are each one of an unsubstituted or substituted C1-C10 monovalent alkyl, olefin, and aryl group, and a disubstituted benzene ring is para-disubstituted or meta-disubstituted, preferably para-disubstituted.

The present invention further provides a method of producing a phenylene disilanol compound with structural formula (I), comprising the steps of: (1) dissolving phenylene disilane with structural formula (A) in a solvent to undergo an alkoxide substitution reaction in a base catalytic environment; (2) providing an aqueous solution for undergoing hydrolysis; and (3) providing an inorganic salt aqueous solution for undergoing neutralization, rinsing it with another solvent, and drying it to obtain a phenylene disilanol compound with structural formula (I).

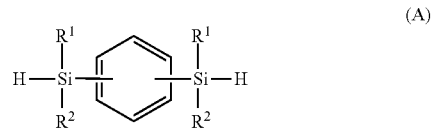

wherein $R^1$ and $R^2$ are each one of an unsubstituted or substituted C1-C10 monovalent alkyl, olefin, and aryl group, and a disubstituted benzene ring is para-disubstituted or meta-disubstituted, preferably para-disubstituted.

Regarding the phenylene disilanol and the method of producing the same, when R1 and $R^2$ are independently methyl, the compound takes on structural formula (I-1):

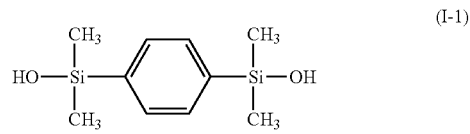

Regarding the method of producing the phenylene disilanol with structural formula (I), step (1) must be carried out in a moisture-free atmosphere. The moisture-free atmosphere is preferably a nitrogen atmosphere or argon atmosphere. The solvent is a anhydrous alcohol-based solvent, preferably methanol. The base catalyst is metallic sodium, sodium methoxide or sodium ethoxide. In step (2), the aqueous solution is a sodium hydroxide aqueous solution. In step (3), the inorganic salt aqueous solution has a pH of 4~10, the aqueous solution is preferably an ammonium chloride aqueous solution, and the other solvent is n-alkane, isoalkane, neoalkane or cycloalkane, preferably n-hexane or n-heptane. According to the present invention, the anhydrous methanol is the sole solvent and is easier to perform distillation than absolute ethanol, not to mention that it does not require tetrahydrofuran, thereby enhancing the feasibility of mass production greatly. After the reacting mixture has undergone hydrolysis with a sodium hydroxide solution, neutralization is carried out with ammonium chloride solution; hence, a high-purity phenylene disilanol product with a yield of at least 80% is obtained without performing intricate aqueous solutions treatment processes, thereby improving the methods of the present invention from an economic perspective.

The raw reactant with structural formula (A) is produced from a dihalobenzene with structural formula (V):

wherein X is bromine atom or iodine atom; when expressed by structural formula (V), dihalobenzene $C_6H_4X_2$ is para-disubstituted or meta-disubstituted, preferably para-disubstituted.

Regarding the phenylene disilane, $R^1$ and $R^2$ are independently methyl, and the compound takes on structural formula (A-1):

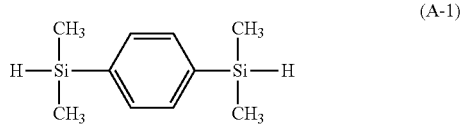
(A-1)

The disilane with structural formula (A-1) is produced in a moisture-free atmosphere. The moisture-free atmosphere is preferably a nitrogen atmosphere or argon atmosphere. The disilane with structural formula (A-1) is produced from reactants, such as 1,4-dibromobenzene (1,4-$C_6H_4Br_2$), metallic magnesium, and dimethylsilyl chloride ($Me_2HSiCl$). The solvent required for the reaction is ether or tetrahydrofuran, preferably tetrahydrofuran. The reaction takes place at a temperature which ranges from 40 to 80° C., preferably 65° C., for 6 to 24 hours, preferably 16 hours. The reacting mixture is blended by a magnet or a mechanical blending device, depending on the reaction dosage.

In order to achieve the above and other objectives, the present invention further provides a polymer with alternating phenylene silicon and siloxane structure. The polymer is expressed by structural formula (II):

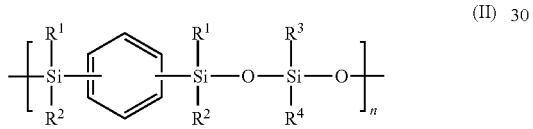
(II)

wherein n is a positive integer which ranges from 4 to 4,000 and denotes the numbers of repeating monomer units which the polymer consists of. The polymer has a weight-average molecular weight which ranges from 1,000 to 800,000, preferably 20,000 to 300,000. $R^1$, $R^2$, $R^3$ and $R^4$ are each independently one of an unsubstituted or substituted C1-C10 monovalent alkyl, olefin, and aryl group, preferably methyl, ethyl, propyl, vinyl, allyl, and phenyl, and most preferably methyl and vinyl. The disubstituted phenylene is para-disubstituted or meta-disubstituted, preferably para-disubstituted.

In order to achieve the above and other objectives, the present invention further provides a method of producing a polymer expressed by structural formula (II) and comprising alternating phenylene silicon and siloxane structure. The method comprises the steps of: (a) polycondensing the compound with structural formula (I) and diamino silane with structural formula (B) in a solvent and in a heating environment; (b) adding, when the polycondensed reactants are gelled, another solvent to the gelled reactants to cool the gelled reactants; and (c) performing centrifugal separation and then drying on a solution obtained in step (b) to obtain the polymer with structural formula (II).

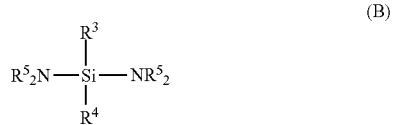
(B)

wherein $R^3$ and $R^4$ are the same or different and are each independently one of an unsubstituted or substituted C1-C10 monovalent alkyl, olefin, and aryl group, and $R^5$ are the same and are each independently one of an unsubstituted or substituted C1-C3 monovalent alkyl, —$(CH_2)_4$—, and —$(CH_2)_5$— cyclic alkyl chain ring.

Regarding the diamino silane, when $R^3$, $R^4$ and $R^5$ are each independently methyl, the diamino silane takes on structural formula (B-1):

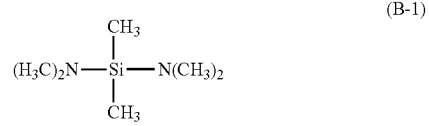
(B-1)

Regarding the diamino silane, when $R^3$, $R^5$ are independently methyl, and $R^4$ is vinyl, the diamino silane takes on structural formula (B-2):

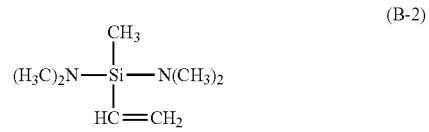
(B-2)

Regarding the polymer with alternating phenylene silicon and siloxane structure and a method of producing the same, when $R^1$, $R^2$, $R^3$ and $R^4$ are each independently methyl, the disubstituted phenylene is para-disubstituted, and the polymer takes on structural formula (II-1):

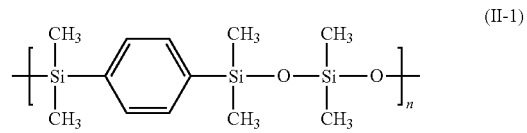
(II-1)

Regarding the polymer with alternating phenylene silicon and siloxane structure and the method of producing the same, when $R^1$, $R^2$ and $R^3$ are each independently methyl, $R^4$ is vinyl, the disubstituted phenylene is para-disubstituted, and the polymer takes on structural formula (II-2):

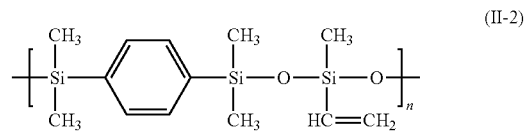
(II-2)

Regarding the method of producing a polymer expressed by structural formula (II) and comprising alternating phenylene silicon and siloxane structure, step (a) is carried out in a moisture-free atmosphere. The moisture-free atmosphere is preferably a nitrogen atmosphere or argon atmosphere. The solvent is toluene or xylene, preferably toluene. Heating is required in the course of the reaction; to this end, the reaction device comprises a temperature control circuit and a built-in temperature sensor. The reaction takes place at a temperature which ranges from 80 to 130° C., preferably 110° C., for 0.5 to 24 hours, preferably 2.5 hours. The reacting mixture is blended by a magnet or a mechanical blending device, depending on the reaction dosage. In step (b), the other solvent is methanol. In step (c), the centrifugal separation takes place at room temperature, with a rotation speed of 6,000~10,000 rpm, preferably 8,000 rpm, for 5~15 minutes, preferably 10 minutes.

Phenylene disilanol monomer compounds are produced by the methods of the present invention, using anhydrous methanol as the solvent, and using ammonium chloride solution to effectuate neutralization, with a simple process flow, achieving a yield of at least 80%. The production of the compounds does not require using carbon tetrachloride or toluene as a solvent for performing recrystallization and purification, but the compounds can directly function as the precursor for use in the synthesis of the polymer with alternating phenylene silicon and siloxane structure. As provided by the present invention, a method of producing a polymer with alternating phenylene silicon and siloxane structure is characterized in that the purification entails applying a simple smart centrifugal separation technique which achieves a yield of at least 80%, a 5% weight loss temperature ($T_{d5}$) of at least 400 to 500° C., and a satisfactory charring residue percentage at 700° C. in the presence of nitrogen. Therefore, as provided by the present invention, a polymer with alternating phenylene silicon and siloxane structure and a method of producing a precursor of the same are characterized by the ease of autonomous synthesis of monomers and a polymer thereof and a simple process flow, economic improvement of mass production, and promotion of the industrial development of non-inflammable silicone polymer materials.

The aforesaid summary, the description below, and accompanying drawings are intended to further explain the measures taken to achieve the objectives of the present invention and the effects thereof. The other objectives and advantages of the present invention are described below with reference to the accompanying drawings.

DETAILED DESCRIPTION OF THE PREFERRED EMBODIMENTS

Features and advantages of the present invention are hereunder illustrated with specific embodiments so as for persons skilled in the art to gain insight into the present invention.

The present invention provides a method of producing a polymer monomer, such as a phenylene disilanol with structural formula (I), which is produced from a raw disilane reactant with structural formula (A). A disilane with structural formula (A-1) is produced from reactants, such as 1,4-dibromobenzene, metallic magnesium, and dimethylsilyl chloride. Hence, the method of producing phenylene disilanol with structural formula (I-1) involves using 1,4-dibromobenzene as a reactant and replacing bromo substituent with silyl group to produce the disilane with structural formula (A-1), and then performing substitution and hydrolysis on the Si—H bond of the disilane, thereby producing phenylene disilanol with structural formula (I-1). The process entails replacing the Si—H bond of silane with alkoxide to form siloxane Si—OR and then using hydroxide ions to carry out hydrolysis so as to form the final silanol Si—OH structure. The anhydrous alkoxide solution is produced by a reaction between metallic sodium and an alcohol; alternatively, sodium methoxide or sodium ethoxide functions as the alkoxide source.

To further produce a polymer with alternating phenylene silicon and siloxane structure, the present invention provides a method of producing, separating, and purifying polymers which are expressed by structural formula (II-1) and structural formula (II-2) and comprise alternating phenylene silicon structure and siloxane structure, and allows the phenylene disilanol expressed by structural formula (I-1) and produced by the method of the present invention and diamino silane monomer expressed by structural formula (B-1) or structural formula (B-2) to undergo alternate, repetitious polycondensation, centrifugal separation, and purification. The disubstituted phenylene is para-disubstituted or meta-disubstituted, preferably para-disubstituted.

Figure 1:
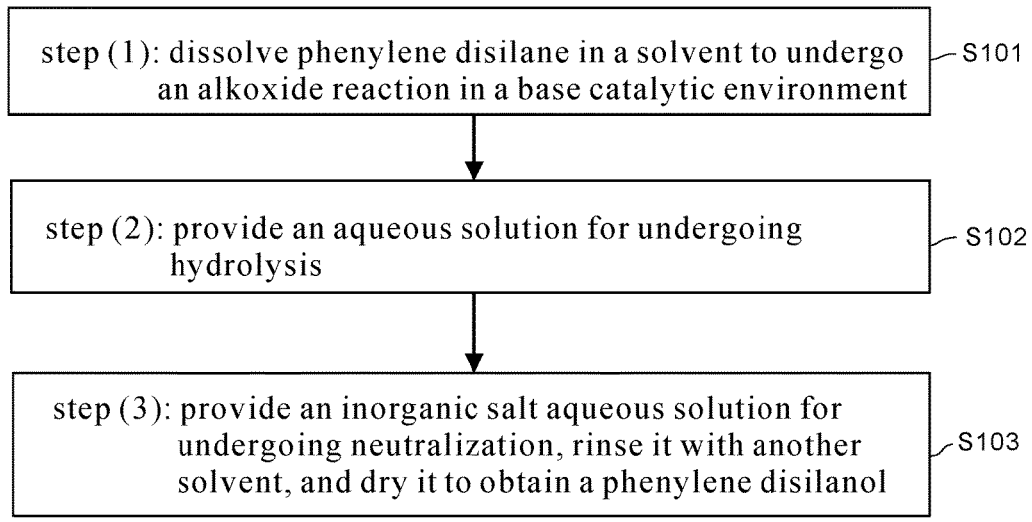
FIG. 1 is a flowchart of a method of producing a precursor of a polymer with alternating phenylene silicon and siloxane structure according to the present invention.
Figure 1:
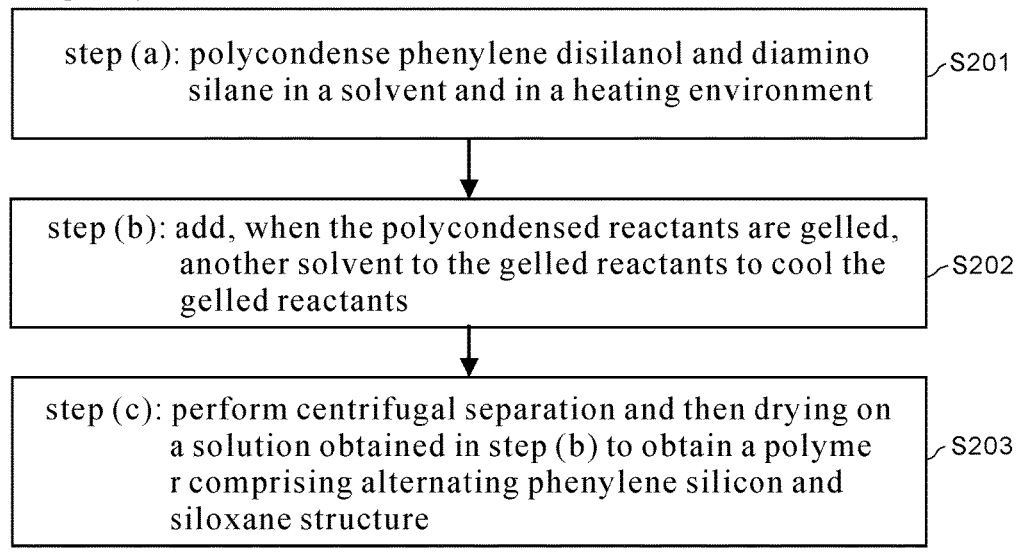
Figure 2:
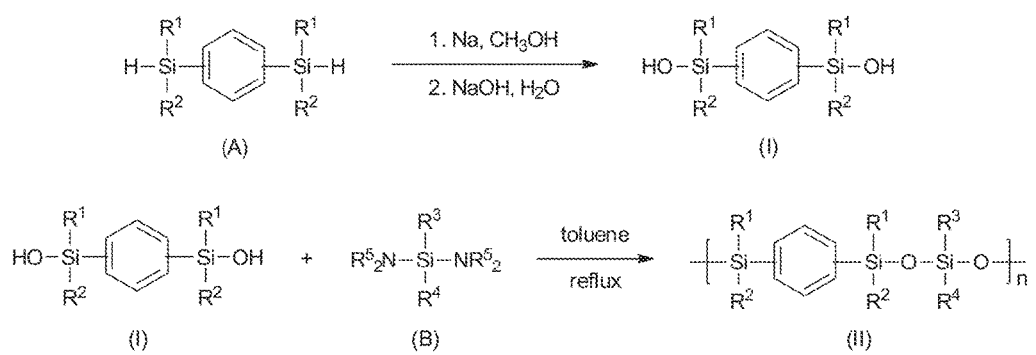
FIG. 2 is a schematic view of the synthesis of phenylene disilanol and a polymer with alternating phenylene silicon and siloxane structure according to an embodiment of the present invention.

Referring to FIG. 1 and FIG. 2, there are shown a flowchart and a schematic view of a method of producing a polymer with alternating phenylene silicon and siloxane structure and a precursor of the polymer according to the present invention, respectively. First, the method entails producing a phenylene disilanol compound with structural formula (I), by following the steps: (1) dissolving phenylene disilane with structural formula (A) in a solvent to undergo an alkoxide reaction in a base catalytic environment; (2) providing an aqueous solution for undergoing hydrolysis; and (3) providing an inorganic salt aqueous solution for undergoing neutralization, rinsing it with another solvent, and drying it to obtain a phenylene disilanol with structural formula (I). The present invention further provides a method of producing a polymer expressed by structural formula (II) and comprising alternating phenylene silicon and siloxane structure, by following the steps: (a) polycondensing the compound with structural formula (I) and diamino silane with structural formula (B) in a heating environment and in a solvent; (b) adding, when the polycondensed reactants are gelled, another solvent to the gelled reactants to cool the gelled reactants; and (c) performing centrifugal separation and then drying on a solution obtained in step (b) to obtain the polymer with structural formula (II).

Embodiment

Figure 3:
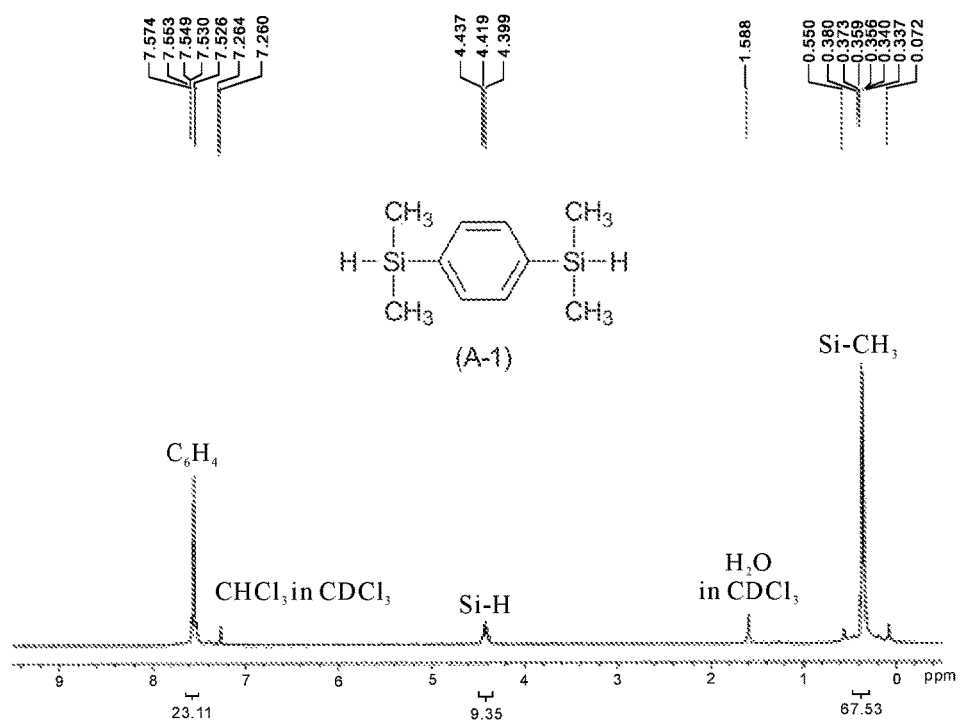
FIG. 3 shows the $^1$H-NMR spectrum for phenylene disilane according to an embodiment of the present invention.

Synthesis of compound (A-1): Setup a reaction device, such as a feeding pipe and a reflux pipe, on a three-necked round bottom flask. Put 6.1 g (0.25 mol) of metallic magnesium in the three-necked round bottom flask. Dry the inside of the three-necked round bottom flask. Introduce nitrogen gas or argon gas into the three-necked round bottom flask. Introduce 20 mL of tetrahydrofuran into the reaction device slowly, cover it fully with metallic magnesium, and stir the reactants. Introduce 27.9 mL (0.25 mmol) of dimethylsilyl chloride (Me$_2$HSiCl) into the reaction device slowly, thereby producing the first solution. Producing the second solution entails introducing 24.7 g (0.11 mol) of dibromobenzene and 60 mL of tetrahydrofuran into the feeding pipe or a dosage transmission pump to blend the dibromobenzene solution. Drip 0.5 mL of the second solution slowly to the first solution in the reaction device, so as to trigger the Grignard reaction. Then, feed the mixed first and second solutions to the reaction device slowly enough to prevent the reacting mixture from boiling; meanwhile, the reaction temperature ranges from 50° C. to 60° C. Afterward, residual dibromobenzene in the feeding pipe is washed into the reaction device by 5~10 mL of tetrahydrofuran to produce the third solution, and then the third solution is heated and refluxed for 16 hours. In the presence of a device temperature sensor, the reflux of tetrahydrofuran requires an internal reaction temperature of 65° C. In the absence of any device temperature sensor, the reflux of tetrahydrofuran requires an oil or sand bath tank temperature of 75° C.~85° C., depending on the size of the reaction device. Upon completion of the reaction, 150 mL of distilled water is slowly introduced into the third solution in the reaction device to trigger a quenching reaction, and then the third solution is stirred continuously for 5~10 minutes to form two layers of immiscible solution known as the fourth solution. Transfer the fourth solution to a separatory funnel to extract the aqueous layer with 60 mL of ether thrice, and then collect the organic supernatant before rinsing it with 100 mL of water and 120 mL of saturated saline solution for the sake of drying. A drying process is performed with anhydrous sodium sulfate, and then filtration is performed so that the filtrate is depressurized and concentrated to obtain 20.4 g of disilane structural formula (A-1), with a yield of 98%. Referring to FIG. 3, it shows the $^1$H-NMR spectrum for phenylene disilane according to an embodiment of the present invention.

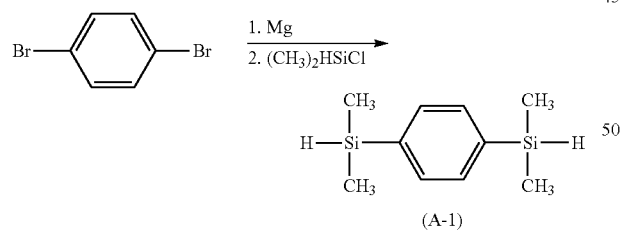

(A-1)

Figure 4:
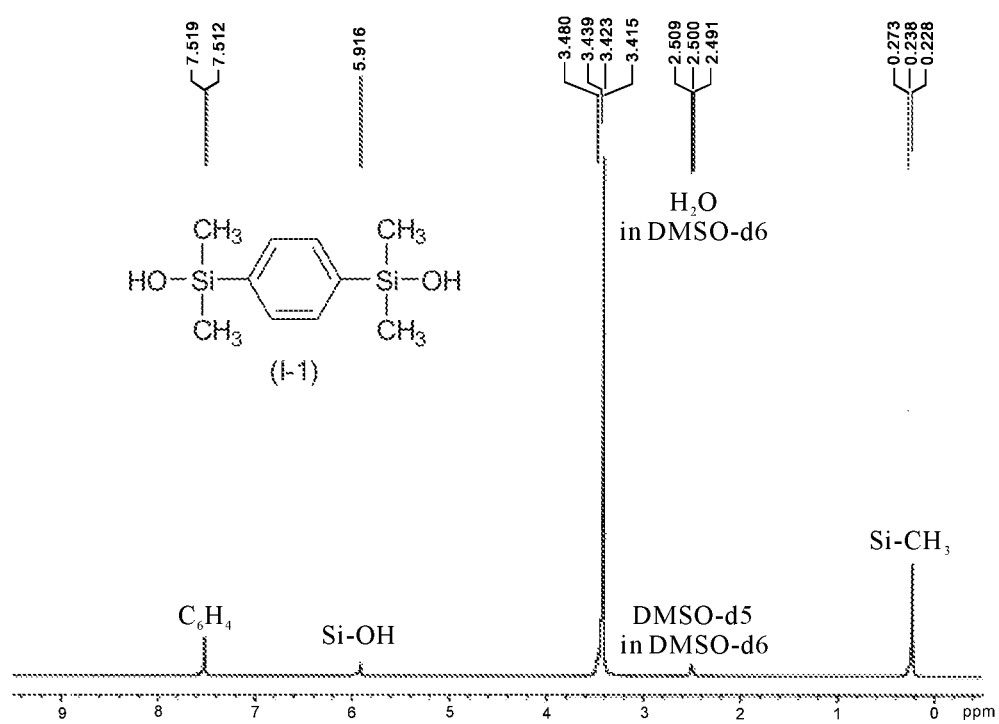
FIG. 4 shows the $^1$H-NMR spectrum for phenylene disilanol according to an embodiment of the present invention.

Synthesis of compound (I-1): Setup a reaction device, such as a reflux pipe, on a two-necked round bottom flask. Dry the inside of the two-necked round bottom flask. Introduce nitrogen gas into the two-necked round bottom flask. Put 250 mL of pre-dried anhydrous methanol in the reaction device. Place the reaction device in an ice water bath. Chips of 6.3 g (274.2 mmol) of metallic sodium are put in the reaction device immersed in the ice water bath under nitrogen gas or argon gas atmosphere one by one and carefully. After the metallic sodium has reacted with methanol completely and no hydrogen bubbles have been generated, the first solution of sodium methoxide is produced. Then, 17.8 g (91.4 mmol) of disilane with structural formula (A-1) and 50 mL of pre-dried anhydrous methanol are introduced into the feeding pipe to form a disilane (expressed by structural formula (A-1)) solution known as the second solution. Drip the second solution slowly to the first solution in the reaction device while hydrogen bubbles are being continuously generated. Afterward, the mixture of first and second solutions are stirred for 10 minutes at room temperature while the generation of hydrogen gas is fading out, thereby producing the third solution. Then, an aqueous solution of a mixture of 11.0 g (274.2 mmol) of sodium hydroxide and 150 mL of water is dripped slowly to the third solution while the third solution is being stirred for 20 minutes, so as to produce the fourth solution. At this point in time, the hydrolysis process is finished, and a saturated ammonium chloride aqueous solution is added to the fourth solution to trigger neutralization therebetween while the fourth solution is being cooled and stirred in an ice water bath for 20 minutes to produce the fifth solution. Transfer the fifth solution to a separatory funnel to undergo extraction with 200 mL of ether thrice, and then collect the organic supernatant before rinsing it with 300 mL of saturated brine solution for the sake of drying. A drying process is performed with anhydrous magnesium sulfate, and then filtration is performed so that the filtrate is depressurized and concentrated to obtain a crude white solid product of phenylene disilanol with structural formula (I-1). Add n-hexane to the crude white solid product of phenylene disilanol with structural formula (I-1) and mix them. Collect the solid precipitate by suction filtration. Rinse the white solid with n-hexane. Collect the white solid product and dry it to obtain 19.1 g of disilanol with structural formula (I-1) at a yield of 92%. Referring to FIG. 4, it shows the $^1$H-NMR spectrum for phenylene disilanol according to an embodiment of the present invention.

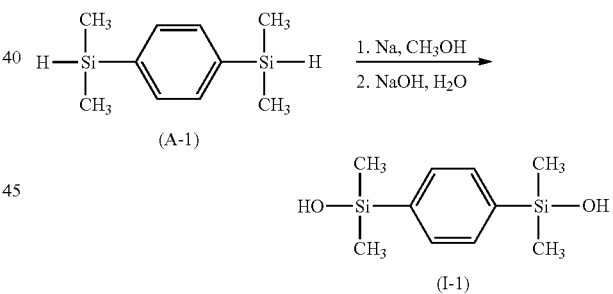

Figure 5:
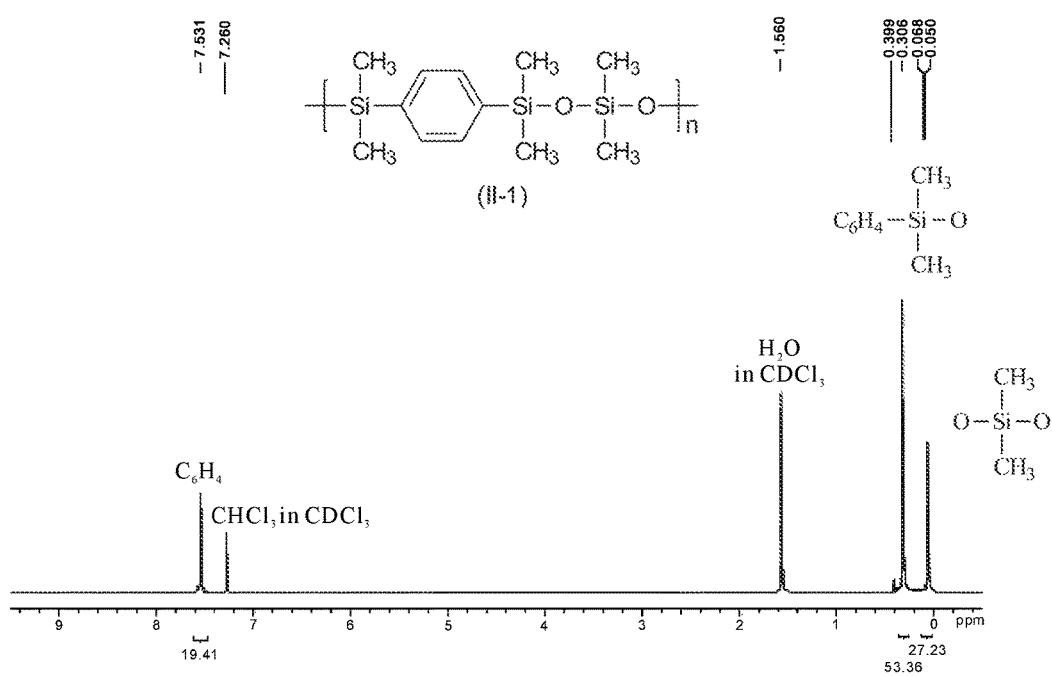
FIG. 5 shows the $^1$H-NMR spectrum for the polymer with alternating phenylene silicon and siloxane structure (II-1) according to an embodiment of the present invention.

Synthesis of polymer (II-1): Setup a reaction device, such as a reflux pipe on a two-necked round bottom flask. Dry the inside of the two-necked round bottom flask. Introduce nitrogen gas or argon gas into the two-necked round bottom flask. Introduce 30.0 g (132.5 mmol) of disilanol with structural formula (I-1) into the two-necked round bottom flask. Add 150 mL of pre-dried anhydrous toluene into the disilanol with a syringe and dissolves it therein to produce the first solution. While being stirred steadily, 19.5 g (133.3 mmol) of diamino silane with structural formula (B-1) is dripped slowly into the reaction device with a feeding funnel, so as to produce the second solution, wherein the mole equivalent ratio of disilanol (I-1) monomer to diamino silane (B-1) monomer is 1.0:1.0. The reacting mixture is put in an oil or sand bath tank and heated therein until reflux occurs, and then the reacting mixture is stirred for one hour. In the presence of a device temperature sensor, the reflux of toluene requires an internal reaction temperature of 110° C. In the absence of any device temperature sensor, the oil or sand bath tank temperature is 120° C.~130° C., depending on the size of the reaction device. After reacting mixture has been stirred for one hour, 20 μL of diamino silane with structural formula (B-1) is dripped into the reaction device every 15 minutes within another one hour so that a total of 80 μL of diamino silane with structural formula (B-1) is dripped into the reaction device. Upon completion of gelation reaction, 50 mL of methanol which has already undergone the ice bath is dripped into the reaction device to end the reaction and thereby produce the third solution. Then, the third solution is depressurized and concentrated to remove the redundant toluene solvent and thus reduce the volume of the concentrated solution to one-fourth of the original volume of the third solution, thereby producing the fourth solution; hence, the precipitation yield of the polymerization product increases. The remaining fourth solution is slowly dripped into 500 mL of methanol which has already undergone the ice bath to promote the precipitation of the polymerization product. Afterward, the underlying gel-state precipitate is separated from the methanol solution above by centrifugal separation so as to remove the supernatant solution. The aforesaid mixing, centrifugal separation, and rinsing processes are repeatedly carried out with 500 mL of methanol (which has already undergone the ice bath) twice. Polymer specimens are collected. The residual solvent is removed by vacuum oven drying performed at 70° C. for 48 hours to obtain a transparent, adhesive-like polymer with structural formula (II-1), that is, 44.5 g of the polymer with alternating phenylene silicon structure and siloxane structure (II-1), with a yield of 90%. Referring to FIG. 5, there is shown the $^1$H-NMR spectrum for the polymer with alternating phenylene silicon and siloxane structure (II-1) according to an embodiment of the present invention.

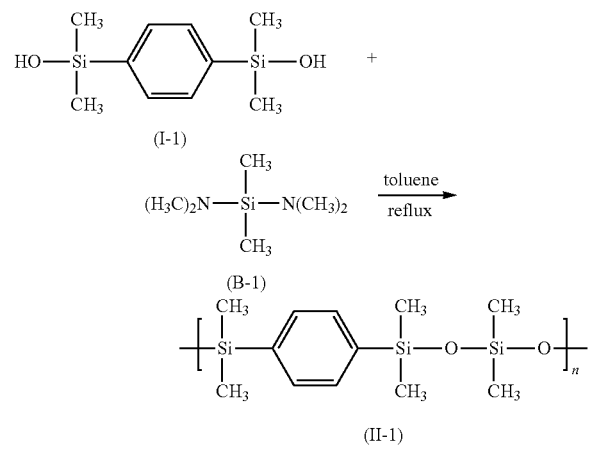

Figure 6:
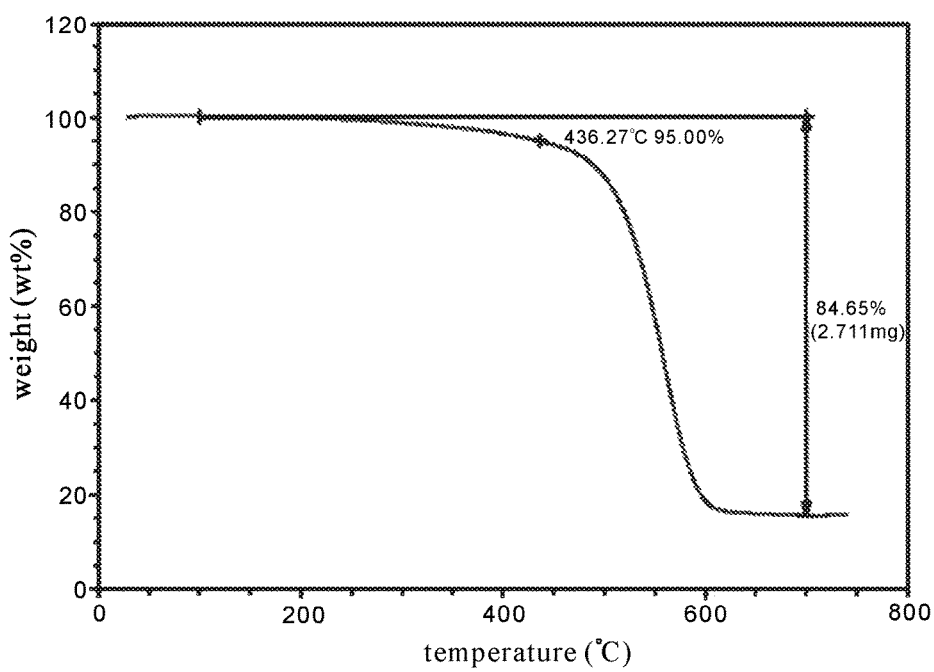
FIG. 6 is a TGA-based graph of weight against temperature for the polymer with alternating phenylene silicon and siloxane structure (II-1) according to an embodiment of the present invention.

Referring to FIG. 6, there is shown a TGA-based graph of weight against temperature for the polymer with alternating phenylene silicon and siloxane structure (II-1) according to an embodiment of the present invention. As shown by the graph, the thermogravimetric analyzer (TGA) performs the analysis and shows that the polymer (II-1) suffers 5% loss of its total weight by pyrolysis at a pyrolysis temperature $T_{d5}$ of 436.3° C. and achieves a charring residual weight ratio of 15.4% in the presence of nitrogen and at 700° C. The molecular weight of the polymerization product is analyzed with gel permeation chromatography (GPC) to show that it has a weight-average molecular weight Mw of 62,800, a number-average molecular weight Mn of 26,000, and a polydispersity index (PDI) of 2.4.

Figure 7:
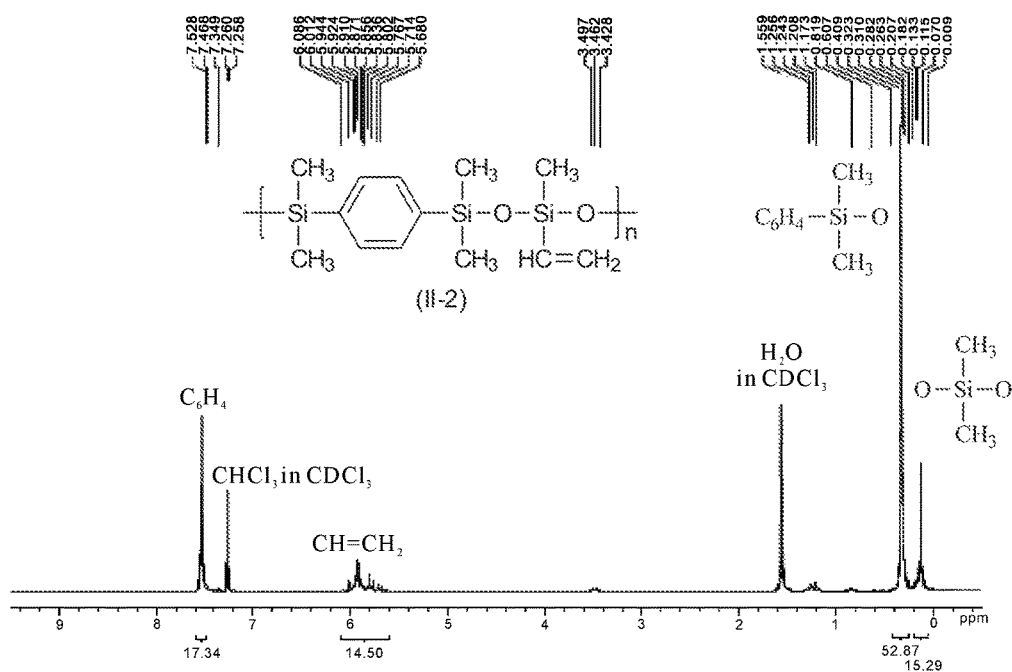
FIG. 7 shows the $^1$H-NMR spectrum for the polymer with alternating phenylene silicon and siloxane structure (II-2) according to an embodiment of the present invention.

Synthesis of polymer (II-2): It requires the same reaction processing method and operation process as disclosed in embodiment 1, but diamino silane with structural formula (B-1) is replaced by diamino silane with structural formula (B-2), wherein the reaction occurs to produce the polymer with structural formula (II-2). In this embodiment, 21.1 g (133.3 mmol) of the diamino silane with structural formula (B-2) is required. In this embodiment, the relative mole equivalent ratio of disilanol monomer with structural formula (I-1) to diamino silane monomer with structural formula (B-2) is 1.0:1.0. Upon completion of the reaction, the resultant polymer with structural formula (II-2) has a yield of 47.0 g (92%). Referring to FIG. 7, there is shown the $^1$H-NMR for the polymer with alternating phenylene silicon and siloxane structure (II-2) according to an embodiment of the present invention.

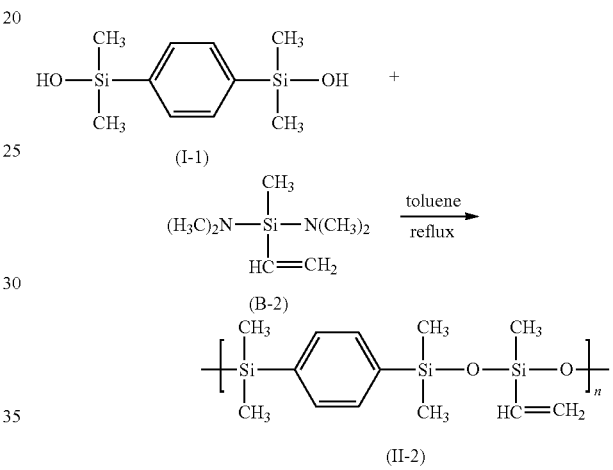

Figure 8:
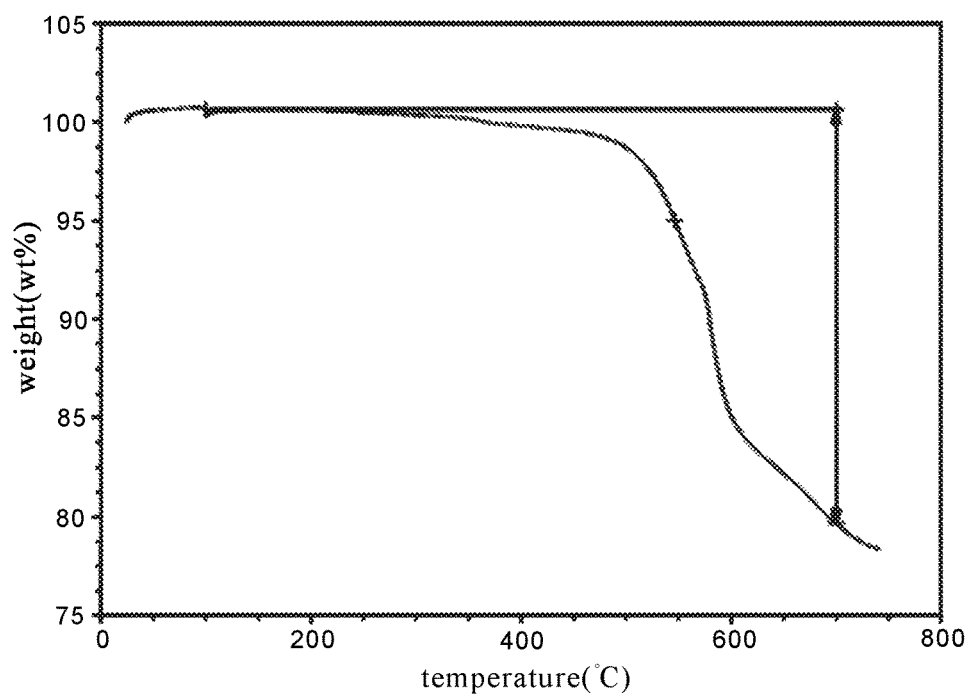
FIG. 8 is a TGA-based graph of weight against temperature for the polymer with alternating phenylene silicon and siloxane structure (II-2) according to an embodiment of the present invention.

Referring to FIG. 8, there is shown a TGA-based graph of weight against temperature for the polymer with alternating phenylene silicon and siloxane structure (II-2) according to an embodiment of the present invention. As shown by the graph, the thermogravimetric analyzer (TGA) performs the analysis and shows that the polymer (II-2) suffers 5% loss of its total weight by pyrolysis at a pyrolysis temperature $T_{d5}$ of 546.7° C. and achieves a charring residual weight ratio of 79.0% in the presence of nitrogen and at 700° C. The molecular weight of the polymerization product is analyzed with gel permeation chromatography (GPC) to show that it has a weight-average molecular weight Mw of 152,300, a number-average molecular weight Mn of 63,300, and a polydispersity index (PDI) of 2.4.

The production of the phenylene disilanol required for producing the polymer with alternating phenylene silicon and siloxane structure and a method of producing a precursor of the same according to the present invention does not require using carbon tetrachloride or toluene as a solvent for performing recrystallization and purification, but can directly function as the precursor for use in the synthesis of the polymer with alternating phenylene silicon and siloxane structure. As provided by the present invention, a method of producing a polymer with alternating phenylene silicon and siloxane structure is characterized in that the purification entails applying a simple smart centrifugal separation technique which achieves a yield of at least 80%, and satisfactory thermal properties, including the polymer's weight loss temperature and charring residue percentage, indicating that the polymer with alternating phenylene silicon and siloxane structure, as produced according to the present invention, meets industrial needs. Therefore, as provided by the present invention, a polymer with alternating phenylene silicon and siloxane structure and a method of producing a precursor of the same are characterized by the ease of autonomous synthesis of monomers and a polymer thereof and a simple process flow, economic improvement of mass production, and promotion of the industrial development of non-inflammable silicone polymer materials, thereby widening their applications.

Although the present invention is disclosed above by preferred embodiments, the preferred embodiments are not restrictive of the present invention. Changes and modifications made by persons skilled in the art to the preferred embodiments without departing from the spirit and scope of the present invention must be deemed falling within the scope of the present invention. Accordingly, the legal protection for the present invention should be defined by the appended claims.

What is claimed is:

1. A method of producing a phenylene disilanol compound, comprising the steps of:
   (1) allowing phenylene disilane with structural formula (A) to undergo an alkoxide reaction in a base catalytic environment and in a waterless methanol solvent;

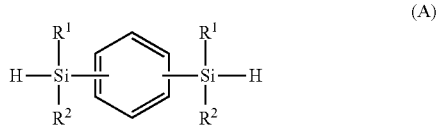

(A)

(2) providing an aqueous solution for undergoing hydrolysis; and
   (3) providing an ammonium chloride aqueous solution for undergoing neutralization, rinsing it with an alkane solvent, followed by drying it to obtain the compound with structural formula (I),

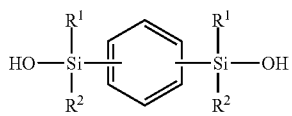

wherein, $R^1$ and $R^2$ are the same or different and are each one of an unsubstituted or substituted C1-C10 monovalent alkyl, olefin, and aryl group, and a disubstituted benzene ring is para-disubstituted or meta-disubstituted.

2. The method of claim 1, wherein, when $R^1$ and $R^2$ are independently methyl, the compound takes on structural formula (I-1).

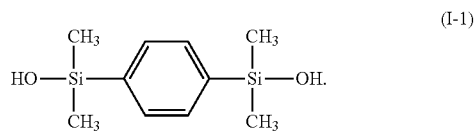

(I-1)

3. The method of claim 1, wherein a base catalyst used in step (1) is one of metallic sodium, sodium methoxide, and sodium ethoxide.

4. The method of claim 1, wherein the aqueous solution in step (2) is a sodium hydroxide aqueous solution.

5. The method of claim 1, wherein the ammonium chloride aqueous solution in step (3) has a pH of 4~10.

6. The method of claim 1, wherein the alkane solvent in step (3) is one of n-alkane, isoalkane, neoalkane, and cycloalkane.

7. The method of claim 6, wherein the n-alkane is one of n-hexane and n-heptane.

8. The method of claim 1, wherein, in step (3), the compound with structural formula (I) has a yield of at least 80%.

9. The method of claim 1, wherein $R^1$ and $R^2$ are the same or different and are each one of methyl, ethyl, propyl, vinyl, acryl, allyl, and phenyl.

* * * * *